United States Patent
Steinmeyer et al.

[11] Patent Number: 5,663,157
[45] Date of Patent: Sep. 2, 1997

[54] 22-EN-25-OXA DERIVATIVES IN THE VITAMIN D SERIES, PROCESS FOR THEIR PRODUCTION, PHARMACEUTICAL PREPARATIONS CONTAINING THESE DERIVATIVES AS WELL AS THEIR USE AS PHARMACEUTICAL AGENTS

[75] Inventors: Andreas Steinmeyer; Gerald Kirsch; Günter Neef; Katica Schwarz; Rüth Thieroff-Ekerdt; Hêrbert Wiesinger; Martin Haberey, all of Berlin, Germany

[73] Assignee: Schering Aktiengesellschaft, Berlin, Germany

[21] Appl. No.: 362,438

[22] PCT Filed: Jun. 30, 1993

[86] PCT No.: PCT/EP93/01735

§ 371 Date: Mar. 16, 1995

§ 102(e) Date: Mar. 16, 1995

[87] PCT Pub. No.: WO94/00429

PCT Pub. Date: Jan. 6, 1994

[30] Foreign Application Priority Data

Jun. 30, 1992 [DE] Germany .......................... 42 21 961.2

[51] Int. Cl.$^6$ .................................................. C07C 401/00
[52] U.S. Cl. ...................................................... 514/167; 552/653
[58] Field of Search ................................ 552/653; 514/167

[56] References Cited

U.S. PATENT DOCUMENTS

| | | | |
|---|---|---|---|
| 4,594,432 | 6/1986 | Baggiolini et al. | 549/214 |
| 4,612,308 | 9/1986 | Baggiolini et al. | 514/167 |
| 4,617,279 | 10/1986 | Manabe et al. | 501/10 |
| 4,711,881 | 12/1987 | Ikekawa | 514/167 |
| 4,719,205 | 1/1988 | DeLuca et al. | 514/167 |
| 4,772,433 | 9/1988 | Hesse | 260/397.2 |
| 4,804,502 | 2/1989 | Baggiolini et al. | 260/397.2 |
| 4,832,875 | 5/1989 | Ikekawa | 260/397.2 |
| 4,851,401 | 7/1989 | DeLuca et al. | 514/167 |
| 4,853,378 | 8/1989 | Hamma et al. | 260/397.2 |
| 4,868,165 | 9/1989 | Ikekawa | 514/167 |
| 4,897,387 | 1/1990 | Ikekawa et al. | 514/167 |
| 4,927,815 | 5/1990 | DeLuca et al. | 514/167 |
| 4,973,721 | 11/1990 | Ikekawa et al. | 552/653 |
| 5,030,626 | 7/1991 | Hamma et al. | 514/167 |
| 5,087,619 | 2/1992 | Baggiolini et al. | 514/167 |
| 5,145,846 | 9/1992 | Baggiolini et al. | 514/167 |
| 5,190,935 | 3/1993 | Binderup et al. | 514/167 |
| 5,194,431 | 3/1993 | DeLuca et al. | 514/167 |
| 5,200,536 | 4/1993 | Ikekawa et al. | 552/653 |
| 5,206,229 | 4/1993 | Calverley et al. | 514/167 |
| 5,206,230 | 4/1993 | Ikekawa et al. | 514/167 |
| 5,210,237 | 5/1993 | Kobayashi et al. | 552/653 |
| 5,260,290 | 11/1993 | DeLuca et al. | 514/167 |
| 5,278,155 | 1/1994 | Ikekawa et al. | 514/167 |
| 5,292,728 | 3/1994 | Neef et al. | 514/167 |
| 5,401,731 | 3/1995 | Calverley et al. | 514/167 |
| 5,401,732 | 3/1995 | Calverley et al. | 514/167 |

OTHER PUBLICATIONS

Antiviral Agents Bulletin, vol. 6 (8), Aug. 1993.
Lavie, et al, *PNAS*, vol. 86, pp. 5963–5967, (Aug. 1989).
Meruelo, et al, *PNAS*, vol. 85, pp. 5230–5234 (Jul. 1988).
Saari, et al, *J. Med Chem*, vol. 35, pp. 3792–3802 (1992).
DeClercq, *Aids Res. & Human Retroviruses*, vol. 8, No. 2, pp. 119–134 (1992).
Letter of Dr. Eric Sandstrom (1992).
Mansuri, et al, *Chemtech*, (Sep. 1992), pp. 564–572.
Connolly, et al, *Antimicrobial Agents & Chemotherapy*, (Feb. 1992) pp. 245–254.
Merck Standby Statement (Sep. 14, 1993).
Antiviral Agents Bulletin, vol. 6(6), Jun. 1993.
*Steroids*, vol. 13, No. 3, pp. 277–312 (1969).

*Primary Examiner*—Kimberly J. Prior
*Attorney, Agent, or Firm*—Millen, White, Zelano, & Branigan, P.C.

[57] ABSTRACT

22-En-24-a-oxa derivatives in the vitamin D series of general formula I

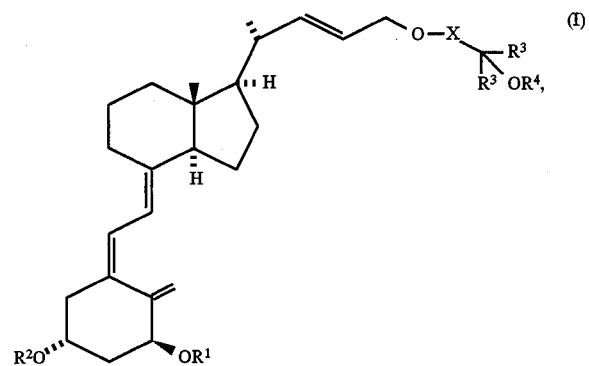

in which $R^1$, $R^2$ and $R^4$, independently of one another, each mean a hydrogen atom, an alkanoyl group with 1 to 9 carbon atoms or an aroyl group, $R^3$ mean a hydrogen atom each or a linear or branched alkyl group each with 1 to 4 carbon atoms, a trifluoromethyl group each or a saturated or unsaturated carbocyclic or heterocyclic 3-, 4-, 5- or 6-membered ring formed together with the tertiary carbon atom, and X means an alkylene radical —$(CH_2)_n$—with n=1, 2 or 3, process for their production and their pharmaceutical use for treating hyperproliferative diseases are disclosed.

16 Claims, No Drawings

22-EN-25-OXA DERIVATIVES IN THE VITAMIN D SERIES, PROCESS FOR THEIR PRODUCTION, PHARMACEUTICAL PREPARATIONS CONTAINING THESE DERIVATIVES AS WELL AS THEIR USE AS PHARMACEUTICAL AGENTS

This application is a 371 of PCT/EP93/01735 filed Jun. 30, 1993, published as WO94/00429, Jan. 6, 1994.

22-En-25-oxa Derivatives in the Vitamin D Series, Process for their Production, Pharmaceutical Preparations Containing these Derivatives as well as their Use as Pharmaceutical Agents This invention relates to 22-en-24a-oxa derivatives in the vitamin D series of general formula I

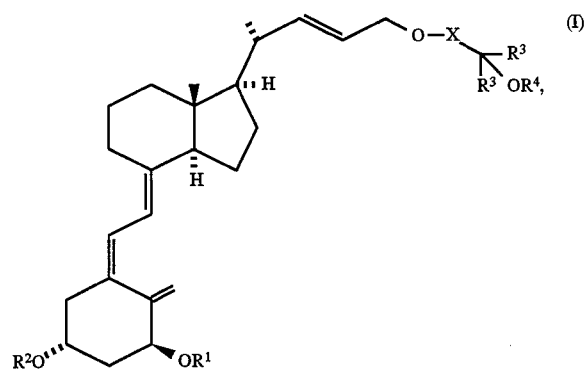

in which $R^1$, $R^2$ and $R^4$, independently of one another, each mean a hydrogen atom, an alkanoyl group with 1 to 9 carbon atoms or an aroyl group, $R^3$ mean a hydrogen atom each or a linear or branched alkyl group each with 1 to 4 carbon atoms, a trifluoromethyl group each or a saturated or unsaturated carbocyclic or heterocyclic 3-, 4-, 5- or 6-membered ring formed together with the tertiary carbon atom, and X means an alkylene radical —$(CH_2)_n$— with n=1, 2 or 3, a process for their production, pharmaceutical preparations that contain these compounds as well as their use for the production of pharmaceutical agents.

The alkanoyl groups possible for radicals $R^1$, $R^2$ and $R^4$ are derived especially from saturated alkanecarboxylic acids and the aroyl group from the benzoic acid.

As alkyl groups for $R^3$, first of all the methyl, ethyl or propyl group or a cyclopropyl or cyclopentyl ring formed together with the tertiary carbon atom are suitable.

Preferred according to this invention are 22-en-25-oxa compounds of general formula I, in which $R^1$, $R^2$ and $R^4$ stand for a hydrogen atom and $R^3$ for a methyl, ethyl or propyl group each and X stands for $CH_2$.

Especially preferred are the compounds:

(5Z,7E,22E)-(1S,3R)-24-(2-Hydroxy-2-methylpropoxy)-9,10-secochola-5,7,10(19),22-tetraene-1,3-diol, (5Z,7E,22E)-(1S,3R)-24-(2-ethyl-2-hydroxybutoxy)-9,10-secochola-5,7,10(19),22-tetraene-,1,3-diol, (5Z,7E,22E)-(1S,3R)-24-(2-hydroxy-2-propylpentoxy)-9,10-secochola-5,7,10(19),22-tetraene-,1,3-diol. 22-en-24b-oxa derivatives in the vitamin D series have already been described (Schering AG, PCT application WO 91/12238).

Natural vitamins $D_2$ and $D_3$ (cf. general formula XV) are biologically inactive per se and are converted to their biologically active metabolites only after hydroxylation in 25-position in the liver or in 1-position in the kidney. The action of vitamins $D_2$ and $D_3$ consists in the stabilization of the plasma-$Ca^{++}$ and plasma-phosphate level; they counteract a decline of the plasma-$Ca^{++}$ level.

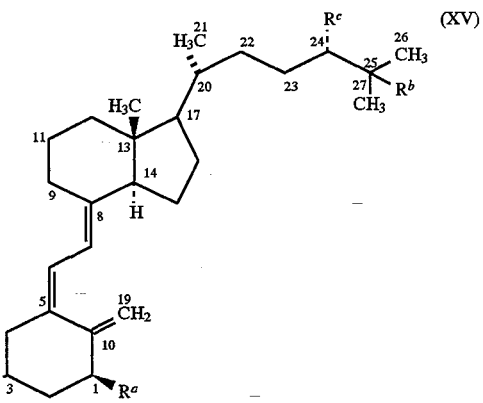

Ergocalciferol: $R^a=R^b=H$, $R^c=CH_3$ Vitamin $D_2$ Double bond C=22/23

Cholecalciferol: $R^a=R^b=R^c=H$ Vitamin $D_3$

25-Hydroxycholecalciferol: $R^a=R^c=H$, $R^b=OH$

1α-Hydroxycholecalciferol: $R^a=OH$, $R^b=R^c=H$

1α,25-Dihydroxycholecalciferol $R^a=R^b=OH$, $R^c=H$ Calcitriol

In addition to their pronounced effect on the calcium and phosphate metabolism, vitamin $D_2$ and $D_3$ and its synthetic derivatives also have proliferation-inhibiting and cell-differentiating effects (H. F. De Luca, The Metabolism and Function of Vitamin D in Biochemistry of Steroid Hormones, Editors H. L. J. Makin, 2nd Edition, Blackwell Scientific Publications 1984, pp. 71–116).

But when using vitamin D, overdosage symptoms can occur (hypercalcemia).

1α-Cholecalciferols hydroxylated in 24-position already follow from DE-AS 25 26 981; they have a lower toxicity than the corresponding nonhydroxylated 1α-cholecalciferol. The hydroxylated compounds show a selective activation of the intestinal calcium absorption and a weaker bone-absorption effect than 1α-cholecalciferol.

The 24-hydroxy-vitamin D analogs described in international patent application WO 87/00834 can be used for the treatment of disorders in humans and animals caused by abnormal cell proliferation and/or cell differentiation.

For various 1,25-dihydroxy-homo-vitamin D derivatives, a dissociation relative to the properties of bone absorption effect and HL-60 cell differentiation has already recently been mentioned by De Luca. The bone absorption effect in vitro is a direct measurement in this case for the calcium mobilization in vivo.

The vitamin D activity of the compounds according to the invention is determined by a calcitriol receptor test. The receptor preparation is obtained from the intestinal mucous membrane of swine (M. C. Dame, E. A. Pierce, H. F. De Luca; Proc. Natl. Acad. Sci. USA 82, 7825 (1985)). Receptor-containing binding protein is incubated in a test tube with calcitriol (0.025 μCi) in a reaction volume of 0.25 ml in the absence and in the presence of the test substance for 2 hours at 4° C. A charcoal-dextran absorption is performed to separate free and receptor-bound calcitriol. To this end, 250 μl of a charcoal-dextran suspension is fed to each test tube, incubated for 20 minutes and centrifuged at 4° C. The supernatant is decanted and after one hour of equilibration in atomic light, measured in a β-counter.

The competition curves obtained with various concentrations of the test substance as well-as of the reference substance (unlabeled calcitriol) at constant concentration of the reference substance ($^3$H-calcitriol) are placed in relation to one another and a competition factor (KF) is determined.

It is defined as a quotient from the concentrations of the respective test substance and the reference substance, which are necessary for 50% competition:

$$KF = \frac{\text{Concentration of test substance at 50\% competition}}{\text{Concentration of reference substance at 50\% competition}}$$

Accordingly, (5Z,7E,22E)-(1S,3R)-24-(2-hydroxy-2-methylpropoxy)-9,10-secochola-5,7,10(19),22-tetraene-1,3-diol (16) has a $K_F$ of 4.4 and (5Z,7E,22E)-(1S,3R)-24-(2-ethyl-2-hydroxybutoxy)-9,10-secochola-5,7,10(19),22-tetraene-1,3-diol (17) has a $K_F$ of 2.0. Both compounds thus bond about as strongly as calcitriol ($K_F$=1) to the vitamin D receptor.

It is known in the literature (D. J. Mangelsdorf et al., J. Cell. Biol. 98: 391–398 (1984)) that the treatment of human leukemia cells (promyelocyte cell line HL 60) in vitro with calcitriol induces the differentiation of the cells to macrophages.

To quantify the differentiation-stimulating effect of calcitriol analogs, the test indicated below is performed:

HL 60 cells are cultivated in tissue-culture medium (RPMI-10% fetal calf serum) at 37° C. in an atmosphere of 5% $CO_2$ in air.

For substance testing, the cells are centrifuged off and $2.8 \times 10^5$ cells/ml in phenol red-free tissue-culture medium are taken up. The test substances are dissolved in ethanol and diluted with tissue-culture medium without phenol red to the desired concentration. The dilution stages are mixed with the cell suspension in a ratio of 1:10 and pipetted in 100 µl each of this cell suspension mixed with substance in an indentation of a 96-hole plate. For control, a cell suspension is analogously mixed with the solvent.

After incubation over 96 hours at 37° C. in 5% $CO_2$ in air, 100 µl of an NBT-TPA solution (nitro blue tetrazolium (NBT), final concentration in the batch of 1 mg/ml, tetradecanoyl phorbol myristate-13-acetate (TPA), final concentration in the batch of $2 \times 10^{-7}$ mol/l) is pipetted in the cell suspension in every indentation of the 96-hole plate.

By incubation over 2 hours at 37° C. and 5% $CO_2$ in air, NBT is reduced to insoluble formazan because of the intracellular oxygen radical release, stimulated by TPA, in the cells differentiated to macrophages.

For completion of the reaction, the indentations of the 96-hole plate are suctioned off, and the adhering cells are fixed by adding methanol and dried after fixing.

To dissolve the formed intracellular formazan crystals, 100 µl of potassium hydroxide (2 val/l) and 100 µl of dimethyl sulfoxide are pipetted in each indentation and ultrasonically treated for 1 minute. The concentration of formazan is measured by spectrophotometry at 650 nm.

The concentration of formed formazan is regarded as a measurement for the differentiation induction of the HL 60 cells to macrophages. The relative effectiveness of the test substance follows from the quotient of $ED_{50}$ test substance/$ED_{50}$ calcitriol.

Accordingly, calcitriol, (5Z,7E,22E)-(1S,3R)-24-(2-hydroxy-2-methylpropoxy)-9,10-secochola-5,7,10(19),22-tetraene-1,3-diol (16) and (5Z,7E,22E)-(1S,3R)-24-(2-ethyl-2-hydroxybutoxy)-9,10-secochola-5,7,10(19),22-tetraene-1,3-diol (17) have the $ED_{50}$ values of $1.6 \times 10^{-9}$ mol/l $3.2 \times 10^{-9}$ mol/l and $1.0 \times 10^{-9}$ mol/l. The substances according to the invention are practically not distinguished from calcitriol in their differentiation-inducing effect.

Calcitriol has a regulating effect on the calcium metabolism. To assess the corresponding activities of the substances according to the invention, the hypercalcemic and hypercalcinuric activity in vivo is determined.

Calcitriol (2 µg/kg) and the test substances (respectively 200 µg/kg) are administered in 500 µl of ethanol/0.9% NaCl solution (40:60 v/v) to subcutaneously intact male Wistar rats (140–160 g), which are fed normally (Altromin™, water). Urine is collected in the period of 0–16 hours after substance administration. Then, the animals orally receive 1 µmol of calcium in 6.5% klucel (hydroxypropyl cellulose) and again urine is collected for the period of 16–22 hours after substance administration. The urine volume of each fraction is measured to measure the absolute calcium excretion.

After 22 hours, the animals are killed by decapitation and the blood is collected. The calcium concentration in serum and urine is determined by flame photometry.

Based on the measured data, the in vivo potency of (5Z,7E,22E)-(1S,3R)-24-(2-hydroxy-2-methylpropoxy)-9,10-secochola-5,7,10(19),22-tetraene-1,3-diol (16) is reduced by more than the factor 100, of (5Z,7E,22E)-(1S,3R)-24-(2-ethyl-2-hydroxybutoxy)-9,10-secochola-5,7,10(19),22-tetraene-1,3-diol (17) by approximately the factor 100 in comparison to calcitriol.

In a dosage of 200 µg/kg, 16 induces no hypercalcemia, 17 induces a slight hypercalcemia, which was comparable with the increase of the calcium concentration in a calcitriol dose of 2 µg/kg (serum calcium concentration: solvent control 3.0 mmol/l calcitriol 3.2 mmol/l, 16 3.0 mmol/l 17 3.4 mmol/l). The calcium excretion was respectively slightly increased in the first collecting phase (0–16 hours) relative to the solvent control but approximately identically with the calcium excretion, which was triggered by calcitriol in a 100-times lower dosage: calcium concentration (first collecting phase): solvent control 12.2 µmol/animal, calcitriol 40.6 µmol/animal, 16 62.4 µmol/animal, 17 61.7 µmol/animal.

In the second collecting phase (16–22 hours), after administration of 17 (200 µg/kg), the calcium excretion was not significantly different to the standard calcitriol (2 µg/kg); the calcium excretion after administration of 16 (200 µg/kg) was not increased relative to the solvent control and thus significantly lower than in calcitriol administration: calcium concentration (second collecting phase): solvent control 1.5 µmol/animal, calcitriol 25.1 µmol/animal, 16 3.6 µmol/animal, 17 47.0 µmol/animal. These findings point to an effect dissociation between growth-inhibiting and calcitropic effect of the test substances in systemic administration in comparison calcitriol.

By the reduced risk of hypercalcemia, the substances according to the invention are especially suitable for producing pharmaceutical agents for the treatment of diseases, which are characterized by a hyperproliferation, e.g., hyperproliferative diseases of the skin (psoriasis) and malignant tumors (leukemia, colon cancer, breast cancer) and acne (J. Invest. Dermatol., Vol. 92, No. 3, 1989).

In an especially preferred embodiment of this invention, calcitriol receptors in the target organ are detected before the treatment with the compounds according to the invention.

Further, it was found that by topical application of the compounds according to the invention on the skin of mice, rats and guinea pigs, an increased reddening of the skin and increase of the thickness of the epidermis can be induced. The increase of the reddening of the skin is determined based on the increase of the red value of the skin surface that can be quantified with a colorimeter. After administering the substance three times at an interval of 24 hours, the red value is clearly increased. The increase of the thickness of the epidermis is quantified in the histological preparation and is also increased.

These properties of the vitamin D compounds according to the invention can appear suitable for therapeutic use in atrophic skin, as it occurs in the natural aging of the skin, premature aging of the skin because of increased exposure to light or medicinally-induced skin atrophy by treatment with glucocorticoids. Further, the healing of wounds can be accelerated by topical application with the new compounds.

The compounds of general formula I according to the invention are also potent inhibitors of the proliferation and interleukin (IL 2)-synthesis of human lymphocytes. Because of the inhibition of the lymphocyte proliferation and IL 2-synthesis in low concentration, the compounds of general formula I according to the invention are suitable for treatment of diseases of the immune system, e.g., diseases of the atopic type (atopic dermatitis, asthma), auto-immune diseases including diabetes mellitus, transplant rejection reactions and AIDS.

For calcitriol, it has been found that because of a receptor-mediated mechanism, it inhibits not only the IL 2-secretion, but also the production of other inflammation-promoting cytokines. Since the compounds of general formula I bind to the receptor approximately just as well as calcitriol, they are suitable for treating inflammatory diseases, such as arthritis, ulcerative colitis and Crohn's disease.

In the treatment of auto-immune diseases, transplant rejection reactions and AIDS, the new compounds of general formula I can advantageously be combined with other immunosuppressively effective substances such as Cyclosporin A and FK 506.

This invention thus also relates to pharmaceutical preparations, which contain at least one compound of general formula I together with a pharmaceutical compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For a topical use, the compounds are advantageously formulated as creams or ointments or in a form of pharmaceutical agent suitable for topical use. Each such formulation can also contain other pharmaceutically compatible and nontoxic additives, such as, e.g., stabilizers, antioxidants, binders, dyes, emulsifiers or flavoring substances. The compounds are advantageously administered by injection or intravenous infusion of suitable sterile solutions or as oral dosage by the alimentary tract or topically in the form of creams, ointments, lotions or suitable transdermal plasters, as is described in EP-A-0387 077.

The daily dose is about 0.1 µg/patient/day-1000 µg (1 mg)/patient/day, preferably 1.0 µg/patient/day-500 µg/patient/day.

The compounds of general formula I, especially also the initial compounds of general formula XIV required for their production, are obtained according to a new process. The invention therefore also relates to a process for the production of the compounds of general formula I.

The initial compounds of general formula XIV required for the production of 22-en-24a-oxa-vitamin D derivatives result on a convergent pathway of synthesis, and the CD part and the A part are synthesized separately.

Initial material for the CD fragment is one of the aldehydes II known in the literature (H. H. Inhoffen et al. Chem. Ber. 91, 780 (1958), Chem. Ber. 92, 1772 (1959), W. G. Dauben et al. Tetrahedron Lett. 30, 677 (1989)),

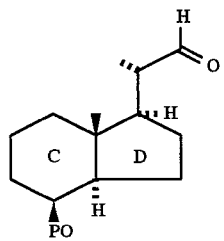

II in which P means an acyl-, alkyl-, aryl- or alkyl- and aryl(mixed)-substituted silyl or tetrahydropyranyl (THP) group. As examples for silyl group P, the tert-butyldimethylsilyl, trimethylsilyl, tert-butyl can be mentioned By Wadsworth-Emmons reaction with the anion of a phosphonate III

$(RO)_2P(O)$—$CH_2$—$COOR'$, (III)

produced by deprotonation with a base (NaH, KH, lithium diisopropylamide (LDA), potassium-tert-butylate), in which R and $R^1$, independently of one another, mean straight-chain or branched alkyl groups with up to 9 carbon atoms or phenyl groups, a compound of general formula IV

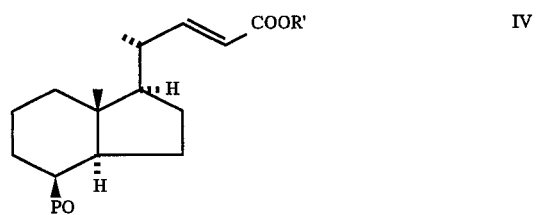

IV is produced, whose ester group is reduced with a reducing agent (LiAlH$_4$, diisobutylaluminum hydride (DIBAH)) to the corresponding alcohol of general formula V.

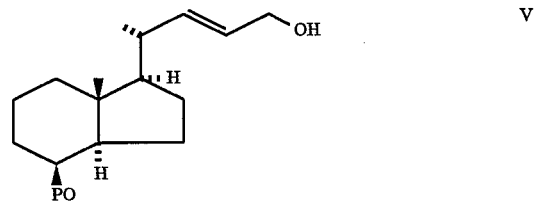

V

By etherification with a compound of general formula VI

L—X—C(O)—OR", (VI)

in which L stands for a leaving group such as Br, I, $CH_3$—$C_6H_4$—$SO_2O$,

X stands for an alkenyl radical —$(CH_2)_n$—with n=1, 2 or 3 and R" stands for a straight-chain or branched alkyl radical with 1 to 8 carbon atoms, a compound of general formula VII is obtained.

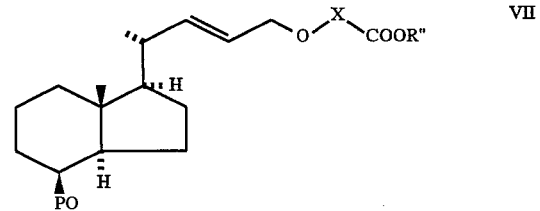

VII

A nucleophilic reagent of general formula VIII $$R^3—M \quad (VIII)$$

is added to its ester group (at least simple excess), in which $R^3$ means a linear or branched alkyl group with 1 to 4 carbon atoms and M means MgHal (Hal=Cl, Br, I) or an alkali atom (Li, Na, K), and a compound of general formula IX is obtained.

If two hydrogen atoms are to stand for $R^3$ in the ultimately desired compound of general formula I, instead of $R^3$—M (VIII), a hydride-yielding reagent, e.g., lithium aluminum hydride, is reacted with VII.

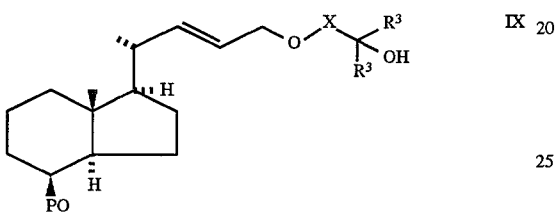

Protective group P in IX is cleaved off. In the case of the acyl group, basic conditions are used ($K_2CO_3$, methanol; KOH or NaOH, methanol) are used; in the case of a silyl protective group, fluoride reagents (tetrabutylammonium fluoride, HF, HF/pyridine) are used; and in the case of the THP protective group, acid catalysis (p-toluenesulfonic acid, pyridinium-p-toluenesulfonate, ion exchanger) is used, so that a compound of general formula X results.

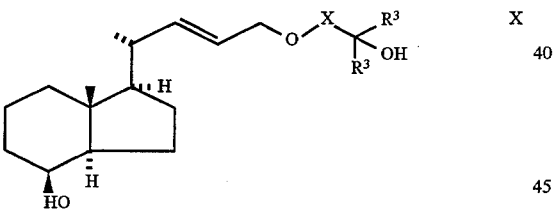

With an oxidizing agent such as pyridinium chlorochromate (PCC), pyridinium dichromate (PDC), Collins reagent or $BaMnO_4$, the secondary hydroxyl group is oxidized to ketone, and a compound of general formula XI results.

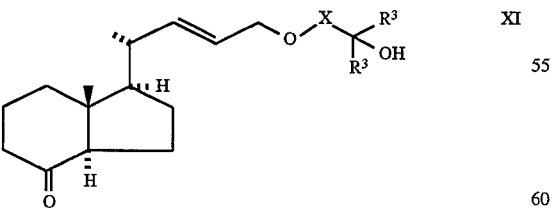

The tertiary hydroxyl group in XI is protected with a hydroxy protective group Z, for example, the trimethylsilyl-, dimethyl-tert-butylsilyl-, an alkyl-aryl-substituted silyl group, the tetrahydropyranyl or tetrahydrofuranyl radical, and a compound of general formula XII results.

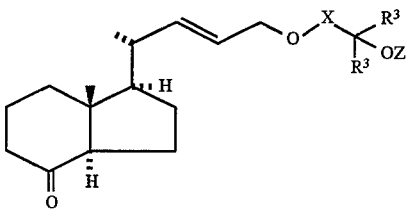

By Horner-Wittig reaction with the anion of the phosphine oxide XIII known in the literature produced by a base such as n-butyllithium or lithium diisopropylamide (BuLi, LDA) (M. R. Uskokovic J. Org. Chem. 51, 3098 (1986))

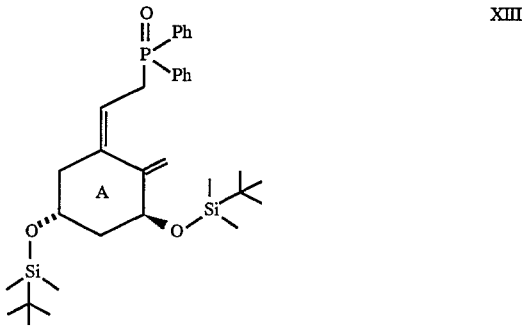

a compound of general formula XIV is obtained.

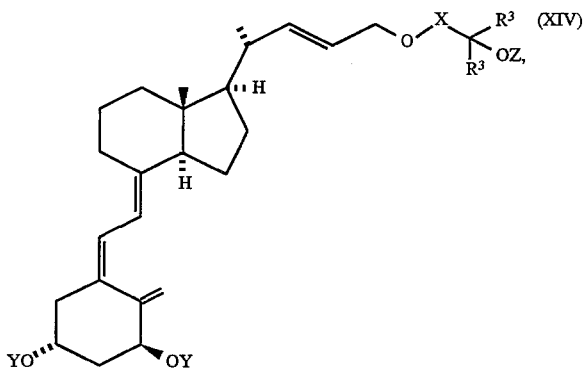

in which Y means respectively a silyl-hydroxy protective group and Z means a silyl, tetrahydropyranyl or tetrahydrofuranyl group as protective group.

By cleaving the protective groups, the compound of general formula XIV is converted to a compound of general formula I, in which $R^1$, $R^2$ and $R^4$ mean hydrogen atoms, and the latter then optionally by esterification of the free hydroxy groups is converted to a compound of general formula I, in which $R^1$, $R^2$ and $R^4$ mean $C_1$-$C_9$ alkanoyl or benzoyl groups.

The cleavage of the hydroxy protective groups takes place preferably by using tetra-n-butylammonium fluoride, HF or HF-pyridine complex.

The possible esterification of free hydroxy groups takes place according to common processes partially, sequentially or completely with the corresponding carboxylic acid halide (halide =chloride, bromide) or carboxylic anhydride.

The following examples are to provide a more detailed explanation of the invention:

EXAMPLE 1

[1R-[1α[R*-(E)],3aβ,4α,7aα]]-4-[4-[[Dimethyl(1,1-dimethylethyl)silyl]oxy]-7a-methyl-octahydro-1H-inden-1-yl]-2-pentenoic acid methyl ester 2

1.55 g (38.7 mmol) of sodium hydride (60%) is introduced in 60 ml of tetrahydrofuran under argon and 7.0 g (38.7 mmol) of dimethyl(methoxycarbonyl)-methylphosphonate is slowly instilled at room temperature in 60 ml of tetrahydrofuran. After 30 minutes at room temperature, 4.1 g (12.6 mmol) of [1R-[1α(S*),3aβ,4α,7aα]]-α,7a-dimethyl-4-[[dimethyl(1,1-dimethylethyl)silyl]oxy]octahydro-1H-indene-1-acetaldehyde 1 (W. G. Dauben et al. Tetrahedron Lett. 30, 677 (1989)) is instilled in 80 ml of tetrahydrofuran and stirred overnight. With ice cooling, saturated sodium chloride solution is now instilled, extracted with ethyl acetate, the organic phase is washed with sodium chloride solution, dried on sodium sulfate and the solvent is removed. The residue is purified chromatographically on silica gel with hexane/ethyl acetate as eluent, and 3.6 g of the title compound is obtained as colorless oil.

$^1$H-NMR (CDCl$_3$): δ=0.01 and 0.03 ppm (2×s; 3H,Si-Me$_2$ each); 0.92 (s,9H,Si-t-butyl); 0.98 (s,3H,H-18); 1.08 (d,J=7 Hz,3H,H-21); 3.72 (s,3H,COOMe); 4.01 (m, 1H,H-8); 5.75 (d,J=15 Hz,1H,H-23); 6.85 (dd,J=15.9 Hz,1H,H-22) [The steroid numbering is used throughout]

IR (film): ν=1720 cm$^{-1}$

EXAMPLE 2

[1R-[1α[R*-(E)],3aβ,4α,7aα]]-4-[4-[[Dimethyl(1,1-dimethylethyl)silyl]oxy]-7a-methyl-octahydro-1H-inden-1-yl]-2-penten-1-ol 3

3.6 g (9.46 mmol) of 2 is introduced in 150 ml of tetrahydrofuran and 37.8 ml of DIBAH (1M in hexane) is instilled under argon at 0° C. It is stirred for 90 minutes at 0° C., sodium chloride solution is added, extracted with ethyl acetate, the organic phase is washed with sodium chloride solution, dried on sodium sulfate and concentrated by evaporation. The residue is purified on silica gel with hexane/ethyl acetate, and 3.0 g of the title compound is obtained as colorless oil.

$^1$H-NMR (CDCl$_3$): δ=0.00 and 0.01 ppm (2×s; 3H,Si-Me$_2$ each); 0.88 (s,9H,Si-t-butyl); 0.95 (s,3H,H-18); 1.02 (d,J=7 Hz,3H,H-21); 4.00 (m, 1H,H-8); 4.08 (sbr,2H,H-24); 5.55 (m,2H,H-22 and H-23)

EXAMPLE 3

[1R-[1α[R*-(E)],3aβ,4α,7aα]]-[[4-[4-[[Dimethyl(1,1-dimethylethyl)silyl]oxy]-7a-methyl-octahydro-1H-inden-1-yl]-2-pentenyl]oxy]acetic acid-1,1-dimethylethylester 4

3.0 g (8.5 mmol) of 3 is dissolved in 3.5 ml of toluene and 39 ml of aqueous sodium hydroxide solution (25%), 545 mg of tetrabutylammonium hydrogen sulfate and 12.08 g (61.9 mmol) of bromoacetic acid-tert-butyl ester are added under argon. It is stirred overnight at room temperature and then mixed with sodium chloride solution. After extraction with ethyl acetate, washing of the organic phase with sodium chloride solution, drying on sodium sulfate and removal of the solvent, the residue is purified chromatographically on silica gel with hexane/ethyl acetate, and 2.3 g of the title compound remains as colorless oil.

$^1$H-NMR (CDCl$_3$): δ=0.00 and 0.02 ppm (2×s; 3H,Si-Me$_2$ each); 0.90 (s,9H,Si-t-butyl); 0.96 (s,3h,H-18); 1.02 (d,J=7 Hz,3H,H-21); 1.50 (s,9H,COO-t-butyl); 3.94 (s,2H,H-26); 4.01 (m, 1H,H-8); 4.02 (d,J=5.5 Hz,2H,H-24); 5.47 (dt,J=15.5,5.5 Hz,1H,H-23); 5.58 (dd,J=15.5,9 Hz,1H,H-22)

EXAMPLE 4

[1R-[1α[R*-(E)],3aβ,4α,7aα]]-1-[[4-[4-[[Dimethyl(1,1-dimethylethyl)silyl]oxy]-7a-methyloctahydro-1H-inden-1-yl]-2-pentenyl]oxy]-2-methyl-2-propanol 5

The Grignard reagent is prepared from 299 mg (12.3 mmol) of magnesium chips and 1.75 g (12.3 mmol) of iodomethane in 10 ml of ether. At 0° C., 1.15 g (2.46 mmol) of 4 is now instilled in 30 ml of ether under argon. It is stirred for 2 hours at room temperature and then hydrolyzed with ammonium chloride solution. After extraction with ethyl acetate, washing of the organic phase with sodium chloride solution, drying on sodium sulfate and removal of the solvent, the crude product is chromatographed on silica gel with hexane/ethyl acetate, and 946mg of the title compound is obtained as colorless oil.

$^1$H-NMR (CDCl$_3$): δ=0.00 and 0.01 ppm (2×s; 3H,Si-Me$_2$ each); 0.90 (s,9H,Si-t-butyl); 0.94 (s,3H,H-18); 1.02 (d,J=7 Hz,3H,H-21); 1.22 (s,6H,H-28 and H-29)); 3.23 (m,2H,H-26); 3.95 (dd,J=12.5,5.5 Hz,1H,H-24); 4.00 (dd,J=12.5,5.5 Hz,1H,H-24'); 4.00 (m, 1H,H-8); 5.42 (dt,J=15.5,5.5 Hz,1H, H-23); 5.53 (dd,J=15.5,9 Hz,1H,H-22)

EXAMPLE 5

[1R-[1α[R*-(E)],3aβ,4α,7aα]]-3-[[[4-[4-[[Dimethyl (1,1-dimethylethyl)silyl]oxy]-7a-methyloctahydro-1H-inden-1-yl]-2-pentenyl]oxy]methyl-3-pentanol 6

The Grignard reagent is prepared from 1.34 g (12.3 mmol) of bromoethane and 299 mg (12.3 mmol) of magnesium chips in 10 ml of tetrahydrofuran and reacted with 4 analogously to example 4. After purification, 1.09 g of the title compound is obtained as colorless oil.

$^1$H-NMR (CDCl$_3$): δ=0.00 and 0.01 ppm (2×s; 3H,Si-Me$_2$ each); 0.89 (t,J=7 Hz,6H,H-30 and H-31); 0.90 (s,9H,Si-t-butyl); 0.94 (s,3H,H-18); 1.02 (d,J=7 Hz,3H,H-21); 1.51 (q,J=7 Hz,4H,H-28 and H-29); 3.27 (m,2H,H-26); 3.92 (dd,J=12.5,5.5 Hz,1H,H-24); 3.98 (dd,J=12.5,5.5 Hz,1H,H-24'); 4.00 (m, 1H,H-8); 5.42 (dt,J-15.5,5.5 Hz,1H,H-23); 5.53 (dd,J=15.5,9 Hz,1H,H-22)

EXAMPLE 6

[1R-[1α[R*-(E)],3aβ,4α,7aα]]-1-[4-(2-Hydroxy-2-methylpropoxy)-1-methyl-2-butenyl]-7a-methyloctahydro-1h-inden-4-ol 7

946 mg (2.22 mmol) of 5 is dissolved in 30 ml of tetrahydrofuran under argon and 5.9 ml of hydrofluoric acid/pyridine complex (70% HF) is added. It is stirred for 48 hours at room temperature and then neutralized with 1n sodium hydroxide solution. After extraction with ethyl acetate, washing of the organic phase with sodium chloride solution, drying on sodium sulfate and removal of the solvent, the residue is purified on silica gel with hexane/ethyl acetate, and 530 mg of the title compound is obtained as colorless oil.

$^1$H-NMR (CD$_2$Cl$_2$): δ=0.90 ppm (s,3H,H-18); 0.96 (d,J=7 Hz,3H,H-21); 1.13 (s,6H,H-28 and H-29); 3.16 (m,2H,H-26); 3.87 (dd,J=12.5,5.5 Hz,1H,H-24); 3.92 (dd,J=12.5,5.5 Hz,1H,H-24'); 3.98 (m, 1H,H-8); 5.39 (dt,J=15.5,5.5 Hz,1H, H-23); 5.47 (dd,J=15.5,9 Hz,1H,H-22)

EXAMPLE 7

[1R-[1α[R*-(E)],3aβ,4α,7aα]]-1-[4-(2-Ethyl-2-hydroxybutoxy)-1-methyl-2-butenyl]-7a-methyloctahydro-1H-inden-4-ol 8

Analogously to example 6, 909 mg (2.01 mmol) of 6 is reacted in 30 ml of tetrahydrofuran with 5.2 ml of hydrofluoric acid/pyridine complex, and 516 mg of the title compound is obtained as colorless oil.

$^1$H-NMR (CDCl$_3$): δ=0.80 ppm (t,J=7 Hz,6H,H-30 and H-31); 0.90 (s,3H,H-18); 0.96 (d,J=7 Hz,3H,H-21); 1.43

(q,J=7 Hz,4H,H-28 and H-29)); 3.18 (m,2H,H-26); 3.85 (dd,J=12.5,5.5 Hz,1H,H-24); 3.90 (dd,J=12.5,5.5H,1H,H-24'); 4.00 (m, 1H,H-8); 5.38 (dt,J=15.5,5.5 Hz,1H,H-23); 5.46 (dd,J=15.5,9 Hz,1H,H-22)

EXAMPLE 8

[1R-[1α[R*-(E)],3aβ,4α,7aα]]-1-[4-(2-Hydroxy-2-propylpentoxy)-1-methyl-2-butenyl]-7a-methyloctahydro-1H-inden-4-ol 9

The Grignard reagent is prepared from 6.15 g (50 mmol) of 1-bromopropane and 1.20 g (50 mmol) of magnesium chips in 50 ml of tetrahydrofuran and reacted with 4 analogously to example 4. The crude product is dissolved again in 60 ml of tetrahydrofuran and reacted with 12.4 ml of hydrofluoric acid/pyridine analogously to example 6, and 1.13 g of the title compound is obtained as colorless oil.

$^1$H-NMR (CDCl$_3$): δ=0.85 ppm (t,J=7 Hz,6H,H-32 and H-33); 0.89 (s,3H,H-18); 0.95 (d,J=7 Hz,3H,H-21); 3.14 (d,J=10 Hz,1H,H-26); 3.19 (d,J=10 Hz,1H,H-26'); 3.83 (dd, J=12.5,5.5 Hz,1H,H-24); 3.89 (dd,J=12.5,7.5 Hz,1H,H-24,'); 4.00 (m, 1H,H-8); 5.36 (dt,J=15.5,6 Hz,1H, H-23); 5.45 (dd,J=15.5,9 Hz,1H,H-22)

EXAMPLE 9

[1R-[1α[R*-(E)],3aβ,7aα]]-1-[4-(2-Hydroxy-2-methylpropoxy)-1-methyl-2-butenyl]-7a-methyloctahydro-4H-inden-4-one 10

530 mg (1.71 mmol) of Z is dissolved in 40 ml of methylene chloride under argon, 538 mg (2.5 mmol) of pyridinium chlorochromate is added and stirred for 90 minutes at room temperature. Then, it is diluted with ether, filtered several times on Celite, and the solvent is removed. The crude product is chromatographed on silica gel with hexane/ethyl acetate, and 446 mg of the title compound remains as colorless oil.

$^1$H-NMR (CDCl$_3$): δ=0.60 ppm (s,3H,H-18); 1.01 (d,J=7 Hz,3H,H-21); 1.13 (s, 6H,H-28 and H-29); 2.40 (dd,J= 10.5,7 Hz,1H,H-14); 3.16 (m,2H,H-26); 3.88 (dd,J=12.5,5.5 Hz,1H,H-24); 3.92 (dd,J=12.5,5.5 Hz,1H,H-24'); 5.40 (dt, J=15.5,5.5 Hz,1H,H-23); 5.49 (dd,J=15.5,9 Hz,1H,H-22)

EXAMPLE 10

[1R-[1α[R,-(E)],3aβ,7aα]]-1-[4-(2-Ethyl-2-hydroxybutoxy)-1-methyl-2-butenyl]-7a-methyloctahydro-4H-inden-4-one 11

Analogously to example 9, 516 mg (1.52 mmol) of 8 is reacted with 478 mg (2.22 mmol) of pyridinium chlorochromate, and 431 mg of the title compound is obtained as colorless oil.

$^1$H-NMR (CDCl$_3$): δ=0.60 ppm (s,3H,H-18); 0.80 (t,J=7 Hz,6H,H-30); 1.01 (d,J=7 Hz,3H,H-21); 1.45 (q,J=7 Hz,H-28 and H-29); 2.40 (dd,J=10.5,7 Hz,1H,H-14); 3.19 (m,2H, H-26); 3.85 (dd,J=12.5,5.5 Hz,1H,H-24); 3.90 (dd,J=12.5, 5.5 Hz,1H,H-24'); 5.39 (dt,J=15.5,5.5 Hz,1H,H-23); 5.48 (dd,J=15.5,9 Hz,1H,H-22)

EXAMPLE 11

[1R-[1α[R*-(E)],3aβ,7aα]]-1-[4-(2-Hydroxy-2-propylpentoxy)-1-methyl-2-butenyl]-7a-methyloctahydro-4H-inden-4-one 12

Analogously to example 9, 1.13 g (3.08 mmol) of 9 is reacted with 966 mg (4.49 mmol) of pyridinium chlorochromate, and 958 mg of the title compound is obtained as colorless oil.

$^1$H-NMR (CDCl$_3$): δ=0.60 ppm (s,3H,H-18); 0.84 (t,J=7 Hz,6H,H-32 and H-33); 1.01 (d,J=7 Hz,3H,H-21); 2.40 (dd,J=10.5,7.5 Hz,1H,H-14); 3.15 (d,J=10 Hz,1H,H-26); 3.19 (d,J=10 Hz,1H,H-26'); 3.84 (dd,J=12.2,5.5 Hz,1H,H-24); 3.89 (dd,J=12.5,5.5 Hz,1H,H-24'); 5.39 (dt,J=15.5,6 Hz,1H,23); 5.48 (dd,J=15.5,9 Hz,1H,H-22)

EXAMPLE 12

[1R-[1α[R*-(E)],3aβ,7aα]]-7a-Methyl-1-[1-methyl-4-[2-methyl-2-[(trimethylsilyl)-oxy]propoxy]-2-butenyl]octahydro-4H-inden-4-one 13

440 mg of 10 is dissolved in 40 ml of ether under argon and 0.46 g (4.2 mmol) of trimethylchlorosilane, 375 mg (5.42 mmol) of imidazole and 0.6 ml of pyridine are added. It is stirred overnight at room temperature and then mixed with sodium chloride solution. After extraction with ethyl acetate, washing of the organic phase with sodium chloride solution and drying on sodium sulfate, the solvent is removed and the crude product is purified by chromatography on silica gel with hexane/ethyl acetate, and 506 mg of the title compound is obtained as colorless oil.

$^1$H-NMR (CDCl$_3$): δ=0.01 ppm (s,9H,Si-Me$_3$); 0.61 (s,3H,H-18); 1.03 (d,J=7 Hz,3H,H-21); 1.15 (s,6H,H-28 and H-29)); 2.40 (dd,J=10.5,7 Hz,1H,H-14); 3.16 (m,2H,H-26); 3.88 (dd,J=12.5,5.5 Hz,1H,H-24); 3.92 (dd,J=12.5,5.5 Hz,1H,H-24'); 5.40 (dt,J=15.5,5.5 Hz,1H,H-23); 5.48 (dd, J=15.5,9 Hz,1H,H-22)

IR (KBr pressed part): ν=1710 cm$^{-1}$

EXAMPLE 13

[1R-[1α[R*-(E)],3aβ,7aα]]-1-[4-[2-Ethyl-2-[(trimethylsilyl)oxy]butoxy]-1-methyl-2-butenyl]-7a-methyloctahydro-4H-inden-4-one 14

Analogously to example 12, 425 mg (1.26 mmol) of 11 is reacted with 411 mg (3.67 mmol) of trimethylchlorosilane, 330 mg (4.77 mmol) of imidazole and 0.53 ml of pyridine, and 474 mg of the title compound is obtained as colorless oil.

$^1$H-NMR (CDCl$_3$): δ=0.00 ppm (s,9H,Si-Me$_3$); 0.59 (s,3H,H-18); 0.74 (t,J=7 Hz,6H,H-30 and H-31); 1.00 (d,J=7 Hz,3H,H-21); 1.43 (q,J=7 Hz,4H,H-28 and H-29)); 2.40 (dd,J=10.5,7 Hz,1H,H-14); 3.14 (m,2H,H-26); 3.87 (dd,J= 12.5,5.5 Hz,1H,H-24); 3.92 (dd,J=12.5,5.5 Hz,1H,H-24,'); 5.40 (dt,J=15.5,5.5 Hz,1H,H-23); 5.49 (dd,J=15.5,9 Hz,1H, H-22)

IR (KBr pressed part): ν=1710 cm$^{-1}$

EXAMPLE 14

1R- [1α[R*- (E)], 3aβ, 7aα]]-7a-Methyl-1-[1-(methyl-4-[2-propyl-2-[(trimethylsilyl) oxy]pentoxy]-2-butenyl]octahydro-4H-inden-4-one 15

Analogously to example 12, 935 mg (2.56 mmol) of 12 is reacted with 803 mg (7.4 mmol) of trimethylchlorosilane, 671 mg (9.7 mmol) of imidazole and 1.01 ml of pyridine, and 857 mg of the title compound is obtained as colorless oil.

$^1$H-NMR (CDCl$_3$): δ=0.00 ppm (s,9H,SiMe$_3$); 0.59 (s,3H, H-18); 0.80 (t,J=7 Hz,6H,H-32 and H-33); 1.00 (d,J=7 Hz,3H,H-21); 2.40 (dd, J=10.5,7.5 Hz,1H,H-14); 3.13 (m,2H,H-26); 3.78 (dd,J=12.5,5.5 Hz,1H,H-24); 3.82 (dd, J=12.5,5.5 Hz,1H,H-24'); 5.39 (dt,J=15.5,5.5 Hz,1H,H-23); 5.48 (dd,J=15.5,9 Hz,1H,H-22)

EXAMPLE 15

(5Z,7E,22E)-(1S,3R)-24-(2-Hydroxy-2-methylpropoxy)-9,10-secochola-5,7,10(19),22-tetraene-1,3-diol 16

83 mg (0.22 mmol) of [3S-(1Z,3α,5β)]-[2-[3,5-bis-[[dimethyl(1,1-dimethylethyl)-silyl]oxy]-2-methylenecyclohexylidene]ethyl]diphenylphosphine oxide (M. R. Uskokovic et al., J. Org. Chem. 51, 3098 (1986)) is dissolved in 2 ml of tetrahydrofuran and cooled under argon to −78° C. Now, 0.185 ml of an n-BuLi solution (1.6 M hexane) is instilled. After 5 minutes, 85 mg (0.22 mmol) of 13 is instilled in 2 ml of tetrahydrofuran and stirred for 30 minutes at this temperature. Then, it is hydrolyzed with potassium-sodium tartrate/potassium hydrogen carbonate solution, extracted with ethyl acetate, the organic phase is washed with sodium chloride solution and dried on sodium sulfate. The solvent is removed and the residue is dissolved under argon in 10 ml of tetrahydrofuran. 0.5 ml (0.5 mmol) of tetrabutylammonium fluoride solution (1M in tetrahydrofuran) is now added and stirred for 60 minutes at 60° C. Then, sodium chloride solution is added, extracted with ethyl acetate, the organic phase is washed with sodium chloride solution, dried on sodium sulfate and the solvent is removed. The residue is purified several times on silica gel with hexane/ethyl acetate, and 10 mg of the title compound is obtained as colorless foam.

$^1$H-NMR (CDCl$_3$): δ=0.59 ppm (s,3H,H-18); 1.06 (d,J=7 Hz, H-21); 1.18 (s,6H,H-28 and H-29); 3.21 (s,2H,H-26); 3.92 (dd,J=15,5.5 Hz,1H,H-24); 3.98 (dd,J=15,5.5 Hz,1H, H-24'); 4.18 (m, 1H,H-3); 4.39 (m, 1H,H-1); 4.96 (s,1H,H-19); 5.30 (s,1H,H-19'); 5.47 (dt,J=15.5,5.5 Hz,1H,H-23); 5.57 (dd,J=15.5,7.5 Hz,1H,H-22); 6.02 and 6.38 (2×d,J=11 Hz; 1H,H-6 and H-7 each)

EXAMPLE 16

(5Z,7E,22E)-(1S,3R)-24-(2-Ethyl-2-hydroxybutoxy)-9,10-secochola-5,7,10(19),22-tetraene-1,3-diol 17

100 mg (0.24 mmol) of 14 is reacted analogously to example 15 with 91 mg (0.24 mmol) of [3S-(1Z,3α,5β)]-[2-[3,5-bis-[[dimethyl(1,1-dimethylethyl)silyl]oxy]-2-methylenecyclohexylidene]ethyl]diphenylphosphine oxide and 0.2 ml of n-BuLi solution and then with 0.54 ml (0.54 mmol) of tetrabutylammonium fluoride solution and after repeated chromatography, 19 mg of the title compound is obtained as colorless foam.

$^1$H-NMR (CDCl$_3$): δ=0.53 ppm (s,3H,H-18); 0.80 (t,J=7 Hz,6H,H-30 and H-31); 1.02 (d,J=7 Hz,3H,H-21); 1.38 (q,J=7 Hz,4H,H-28 and H-29); 3.12 (m,2H,H-26); 3.80 (s,1H,tert-OH); 3.83 (dd,J=15,5.5 Hz,1H,H-24); 3.90 (dd,J=15,5.5 Hz,1H,H-24');4.00 (m, 1H,H-3); 4.20 (m, 1H,H-1); 4.42 (d,J=4 Hz,1H,OH); 4.72 (d,J=5 Hz,1H,OH); 4.77 (s,1H,H-19); 5.21 (s,1H,H-19'); 5.42 (dt,J=15.5,5.5 Hz,1H,H-23); 5.54 (dd,J=15.5,7.5 Hz,1H,H-22); 5.98 and 6.18 (2×d,J=11 Hz; 1H,H-6 and H-7 each)

EXAMPLE 17

(5Z,7E,22E)-(1S,3R)-24-(2-Hydroxy-2-(propylpentoxy)-9,10-secochola-5,7,10(19),22-tetraene-1,3-diol 18

116 mg (0.24 mmol) of 15 is reacted analogously to example 15 with 300 mg (0.53 mmol) of [3S-(1Z,3α,5β)]-[2-[3,5-bis-[[dimethyl(1,1-dimethylethyl)silyl]oxy]-2-methylenecyclohexylidene]ethyl]diphenylphosphine oxide and 0.2 ml of n-BuLi solution and then with 1.0 ml (1.0 mmol) of tetrabutylammonium fluoride solution and after repeated chromatography, 59 mg of the title compound is obtained as colorless foam.

$^1$H-NMR (CD$_2$Cl$_2$): δ=0.58 (s,3H,H-18); 0.90 (t,J=7 Hz,6H,H-32 and H-33); 1.05 (d,J=7 Hz,3H,H-21); 3.20 (d,J=10 Hz,1H,H-26); 3.25 (d,J=10 Hz,1H,H-26'); 3.90 (dd, J=12.5,5.5 Hz,1H,H-24); 3.96 (dd,J=12.5,5.5 Hz,1H,H-24'); 4.18 (m, 1H,H-3); 4.39 (m, 1H,H-1); 4.97 (s,1H,H-19); 5.30 (s,1H,H-19'); 5.46 (dt,J=15.5,6 Hz,1H,H-23); 5.56 (dd,J= 15.5,7.5 Hz,1H,H-22); 6.02 and 6.38 (2×d,J=11 Hz; 1H,H-6 and H-7 each).

We claim:

1. A 22-en-24a-oxa derivative in the vitamin D series of formula I

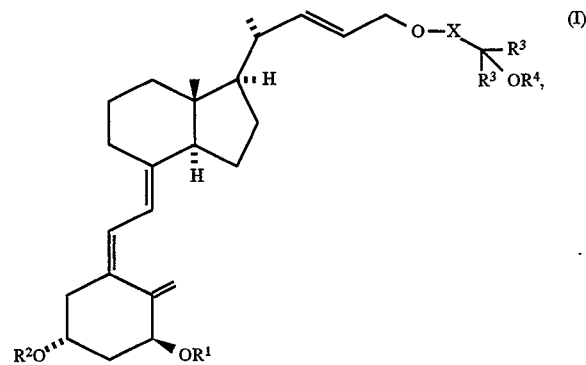

wherein

R, R$^2$ and R$^4$, each independently of one another, is H, a C$_{1-9}$-alkanoyl group or an aroyl group, R$^3$ is a hydrogen atom each or a linear or branched C$_{1-4}$-alkyl group, a trifluoromethyl group each or a saturated or unsaturated carbocyclic or heterocyclic 3-, 4-, 5- or 6-membered ring formed together with the tertiary carbon atom, and X is an alkylene radical —(CH$_2$)$_n$—with n=1, 2 or 3.

2. A 22-en-24a-oxa derivative of claim 1, wherein R$^1$, R$^2$ R$^4$ are each independently H, a C$_{1-9}$-alkanoyl group or a benzoyl radical.

3. A 22-en-24a-oxa derivative of claim 1, wherein both R$^3$s are methyl, ethyl or propyl groups.

4. A 22-en-24a-oxa derivative of claim 1, wherein both R$^3$s together with the tertiary carbon atom to which they are attached are a cyclopropyl or cyclopentyl ring.

5. A 22-en-24a-oxa derivative of claim 1, wherein R$^1$, R$^2$ and R$^4$ each are a hydrogen atom and the R$^3$s each are a methyl, ethyl or propyl group and X is a methylene group (CH$_2$).

6. A pharmaceutical preparation, comprising an effective amount of a compound of claim 1 and a pharmaceutically compatible vehicle.

7. A method of treating hyperproliferative diseases, comprising administering to a patient in need of such treatment an effective amount of a compound of claim 1.

8. A method of claim 7, wherein the disease is psoriasis.

9. A method of claim 7, wherein the disease is a malignant tumor.

10. A method of treating acne, comprising administering to a patient in need of such treatment an effective amount of a compound of claim 1.

11. A method of treating atopic dermatitis or asthma, comprising administering to a patient in need of such treatment an effective amount of a compound of claim 1.

12. A method of treating diabetes mellitus, comprising administering to a patient in need of such treatment an effective amount of a compound of claim 1.

13. A method of treating transplant rejection reaction, comprising administering to a patient in need of such treatment an effective amount of a compound of claim 1.

14. (5Z,7E,22E)-(1S,3R)-24-(2-Hydroxy-2-methylpropoxy)-9,10-secochola-5,7,10(19), 22-tetraene-1,3-diol;

(5Z, 7E,22E)-(1S,3R)-24-(2-ethyl-2-hydroxybutoxy)-9,10-secochola-5,7,10(19),22-tetraene-1,3-diol; or (5Z,7E,22E)-(1S,3R)-24-(2-hydroxy-2-propylpentoxy)-9,10-secochola-5,7,10(19),22-tetraene-1,3-diol.

15. A process for the production of a 22-en-24a-oxa derivative of formula I of claim 11, comprising converting a compound of formula XIV

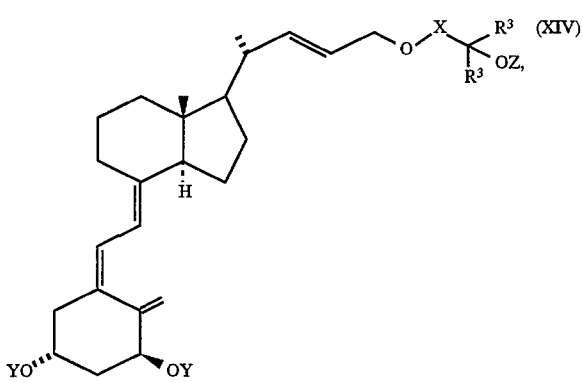

wherein

Y is a silyl-hydroxy protective group and

Z is a silyl, tetrahydropyranyl or tetrahydrofuranyl protective group, by cleaving the protective groups to a compound of formula I, wherein $R^1$, $R^2$ and $R^4$ are hydrogen atoms, and then, optionally, converting the latter by esterification of the free hydroxy groups to a compound of formula I, wherein $R^1$, $R^2$ and $R^4$ are $C_1$-$C_9$-alkanoyl or benzoyl groups.

16. A process of claim 15, wherein the cleavage of the protective groups is performed with tetra-n-butylammonium fluoride/HF or HF-pyridine complex.

* * * * *